United States Patent
Bowman et al.

(10) Patent No.: US 6,265,444 B1
(45) Date of Patent: *Jul. 24, 2001

(54) OPHTHALMIC COMPOSITION

(75) Inventors: Lyle M. Bowman, Pleasanton; James F. Pfeiffer, Oakland; Eric B. Memarzadeh, San Carlos; Samir Roy, San Ramon, all of CA (US)

(73) Assignee: InSite Vision Incorporated, Alameda, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/074,419

(22) Filed: May 8, 1998

Related U.S. Application Data

(63) Continuation-in-part of application No. 08/863,015, filed on May 23, 1997.

(51) Int. Cl.[7] .................................................. A61K 31/19
(52) U.S. Cl. ............................................. 514/570; 514/912
(58) Field of Search ..................................... 514/91 L, 570

(56) References Cited

U.S. PATENT DOCUMENTS

| | | |
|---|---|---|
| 4,559,343 | 12/1985 | Han et al. . |
| 4,829,088 | 5/1989 | Doulakas . |
| 4,960,799 | 10/1990 | Nagy . |
| 5,102,666 | 4/1992 | Acharya . |
| 5,110,493 | 5/1992 | Cherng-Chyi et al. . |
| 5,171,566 | 12/1992 | Mizushima et al. . |
| 5,192,535 | 3/1993 | Davis et al. . |
| 5,296,228 | 3/1994 | Chang et al. . |
| 5,340,572 | 8/1994 | Patel et al. . |
| 5,576,028 | 11/1996 | Martin et al. . |

FOREIGN PATENT DOCUMENTS

| | | |
|---|---|---|
| 28 39 752 | 11/1977 | (DE) . |
| WO 94/10976 | 5/1994 | (WO) . |
| WO 95/31968 | 11/1995 | (WO) . |

OTHER PUBLICATIONS

Laszlo Borka, The Polymorphism Of Indomethacine, *ACTA Pharm. Suecica* 11., pp. 295–303 (1974).

P.S. Weisweiler, et al., *Journal Of Clinical Research and Drug Development*, Dec. 1998, vol. 2, No. 4, pp. 234–238.

*International Journal of Pharmaceutics*, 1989, vol. 55/2.3, pp. 124–128.

Patent Abstracts of Japan, vol. 8, No. 7 (C–204) corresponding to JP58–174309 published Oct. 1983 entitled *Antiphlogistic Eye Drop*.

Derwent Publications Ltd., Section Ch, Week 8347, AN 83–823242, XP002078183 for (JP 58 174309 A) Wakamoto Pharm Co Ltd, Oct. 13, 1983.

*Primary Examiner*—Zohreh Fay
(74) *Attorney, Agent, or Firm*—Arnold & Porter

(57) ABSTRACT

An ophthalmic composition containing a divalent salt and a non-steroidal anti-inflammatory agent as a precipitate. The composition reduces or eliminates the risk of stinging and burning the eye from topical application. Additionally a preservative system comprising a perborate salt, a polyphosphonic acid peroxy stabilizer and EDTA provides stable preservation of a variety of aqueous ophthalmic compositions.

31 Claims, 1 Drawing Sheet

OPHTHALMIC COMPOSITION

This application is a Continuation-in-Part of prior co-pending application Ser. No. 08/863,015, filed May 23, 1997, the entire contents of which are incorporated herein by reference.

BACKGROUND OF THE INVENTION

1. Field of the Invention

The present invention relates to ophthalmic compositions and more particularly, to ophthalmic compositions containing a divalent cation and a non-steroidal anti-inflammatory agent and/or to ophthalmic compositions containing a preservative system.

2. Description of the Related Art

Non-steroidal anti-inflammatory agents can be used in a variety of ophthalmic treatments such as for treating ocular tissue inflammation and its associated pain. Additional uses include (i) preventing particular side-effects from surgical trauma (e.g., on the pupil preventing surgical meiosis), (ii) preventing fluid accumulation in the back of the eye after cataract surgery (post-surgical macular edema) and (iii) preventing the appearance of inflammatory cells and vessel leakage in the anterior chamber. Diclofenac, suprofen, and flurbiprofin are specific examples of non-steroidal anti-inflammatory agents that have been used for the treatment of postoperative inflammation in patients who have undergone cataract extraction. Topical application of non-steroidal anti-inflammatory agents in the eye also appears to relieve some of the itching due to allergic conjunctivitis.

In the past, anti-inflammatory agents, in general, have been administered in solutions at neutral pH. Injection of anti-inflammatory agents in the form of a suspension has also been proposed. Suspensions have been used for topical ophthalmic applications when the drug is not very soluble. However, when the drug is soluble, at an acceptable pH, solutions are normally used to avoid potential irritation caused by the particles of the suspension. The following patents illustrate ophthalmic solutions containing non-steroidal anti-inflammatory agents, including diclofenac.

U.S. Pat. No. 4,960,799 to Nagy concerns a storage stable aqueous solution of sodium ortho-(2,6-dichlorophenyl) aminophenylacetate acid, which is the chemical name for diclofenac sodium, for topical treatment of ocular inflammation. The solution taught by Nagy has a pH of about 7.0 to 7.8.

U.S. Pat. No. 4,829,088 to Doulakas also relates to an ophthalmic medicament containing diclofenac sodium in aqueous solution. The solution contains 2-amino-2-hydroxymethyl-1,3-propanediol as a preservative.

U.S. Pat. No. 5,110,493 to Cherng-Chyi et al. relates to ophthalmic non-steroidal anti-inflammatory drug formulations containing a quaternary ammonium preservative and a non-ionic surfactant.

Patent Abstracts of Japan, Vol. 8, No. 7, Abs. Gp. C-204, concerning Japanese published application 58-174309 (pub. Oct. 13, 1983) relates to an antiphlogistic eye drop composition containing (1) a non-steroidal antiphlogistic agent having a carboxyl group in its structure and (2) a physiologically permissible calcium or magnesium salt. The salt is described as an irritation mitigating agent and is normally added in an amount of 1–1.5 mol per 1 mol of the non-steroidal agent. Sodium diclofenac is specifically mentioned as the non-steroidal antiphlogistic agent and the pH of the composition is preferably maintained in the 7–8 range.

However, a problem with the use of non-steroidal anti-inflammatory agents, as recognized in the above-mentioned Japanese published application, is that stinging or burning sensations are commonly experienced during the first few minutes after topical administration on the eye. Not only are patients who experience such stinging likely to avoid regularly taking their medication, they also receive less benefit from each application. Specifically, the stinging causes tearing which washes away the drug. Having physically removed a portion of the drug from the eye by tearing, the bioavailability of the drug is reduced.

In addressing the stinging problem, it has been proposed to supply a portion of the non-steroidal anti-inflammatory agent in suspension form, as is described in commonly assigned co-pending application Ser. No. 08/248,500, filed May 24, 1994 (the entire contents of which are hereby incorporated by reference). The particle must dissolve before it can treat the eye. By providing some of the active agent as a particle, the flow of the drug onto the eye is delayed; i.e., providing some of the active agent as a particle reduces the initial concentration of the drug contacting the eye. This delay in drug delivery contrasted with the prior compositions wherein all of the agent was in solution, owing to a pH of 7–8, thereby immediately providing to the cornea a high concentration of the drug. The high concentration of the drug on the eye was believed to aggravate the burning and stinging effects of the drug.

While some improvements have been made with respect to the stinging problem by such a technique, there is still a segment of the population that will experience stinging when topically administering non-steroidal anti-inflammatory ophthalmic compositions. Accordingly, further improvements are desirable.

Additionally, preserving an ophthalmic composition that contains a non-steroidal anti-inflammatory agent can be problematic. Conventional broad spectrum antimicrobial agents like benzalkonium chloride (BAK) tend to interact with the non-steroidal anti-inflammatory agents over time and thereby reduce the efficacy of the medication. Indeed, as a general matter, preservatives in ophthalmic compositions are not entirely satisfactory. Effective, broad spectrum anti-microbials tend to reduce the storage stability of the composition and/or have adverse interactions with other components.

A useful preservative system that seeks to overcome some of these deficiencies is disclosed in U.S. Pat. Nos. 5,576,028 and 5,607,698. These systems use a low amount of hydrogen peroxide, or a hydrogen peroxide source, as a preservative in combination with a peroxy stabilizer. The stabilizer is preferably a phosphonic acid such as diethylene triamine penta (methylene-phosphonic acid) and the like which are commercially available from Monsanto under the DEQUEST brand name. Although this system is quite useful, certain improvements in storage stability would be desirable.

SUMMARY OF THE INVENTION

It is an object of the present invention to provide an ophthalmic composition that contains a topically effective amount of a non-steroidal anti-inflammatory agent and that is no more irritating than conventional eye drops.

It is another object of the present invention to provide a non-steroidal anti-inflammatory agent-containing ophthalmic composition that can be taken by a large segment of the population without experiencing stinging or irritation.

A further object of the present invention is to provide a preserved ophthalmic composition that exhibits good stability during storage.

Another object of the present invention is to provide a method for treating diseases of the eye, including inflammation, by topically applying to eyes in need of such treatment a non-steroidal anti-inflammatory agent-containing ophthalmic composition.

Preferred forms of the invention contemplated accomplish at least some of the above objects. One embodiment of the invention is an ophthalmic composition comprising an aqueous medium containing an effective amount of a non-steroidal anti-inflammatory agent, wherein at least about 80 mol. % of said agent is in the form of a precipitate, and at least about 0.5 equivalents of a pharmacologically acceptable divalent cation per mole of said non-steroidal anti-inflammatory agent; said aqueous medium having a pH of from about 4.0 to 6.7. Another embodiment of the invention relates to a method for treating an eye, which comprises administering to an eye in need thereof an effective amount of such an ophthalmic composition. A further aspect of the present invention relates to a method for making such an ophthalmic composition. Another preferred embodiment of the present invention relates to an ophthalmic composition that is formed by combining at least (1) sodium diclofenac, (2) a divalent metal salt, (3) a water insoluble, water-swellable polymer, and (4) water.

A further embodiment of the invention is an ophthalmic composition which comprises water, about 0.01 to 0.5 wt. % of a perborate salt, about 0.001 to 0.06 wt. % of a polyphosphonic acid peroxy stabilizer, and about 0.01 to 0.1 wt. % of ethylenediaminetetraacetic acid. The composition in this embodiment may further comprise a pharmaceutically active agent such as a non-steroidal anti-inflammatory agent.

DETAILED DESCRIPTION OF THE INVENTION

Figure 1:
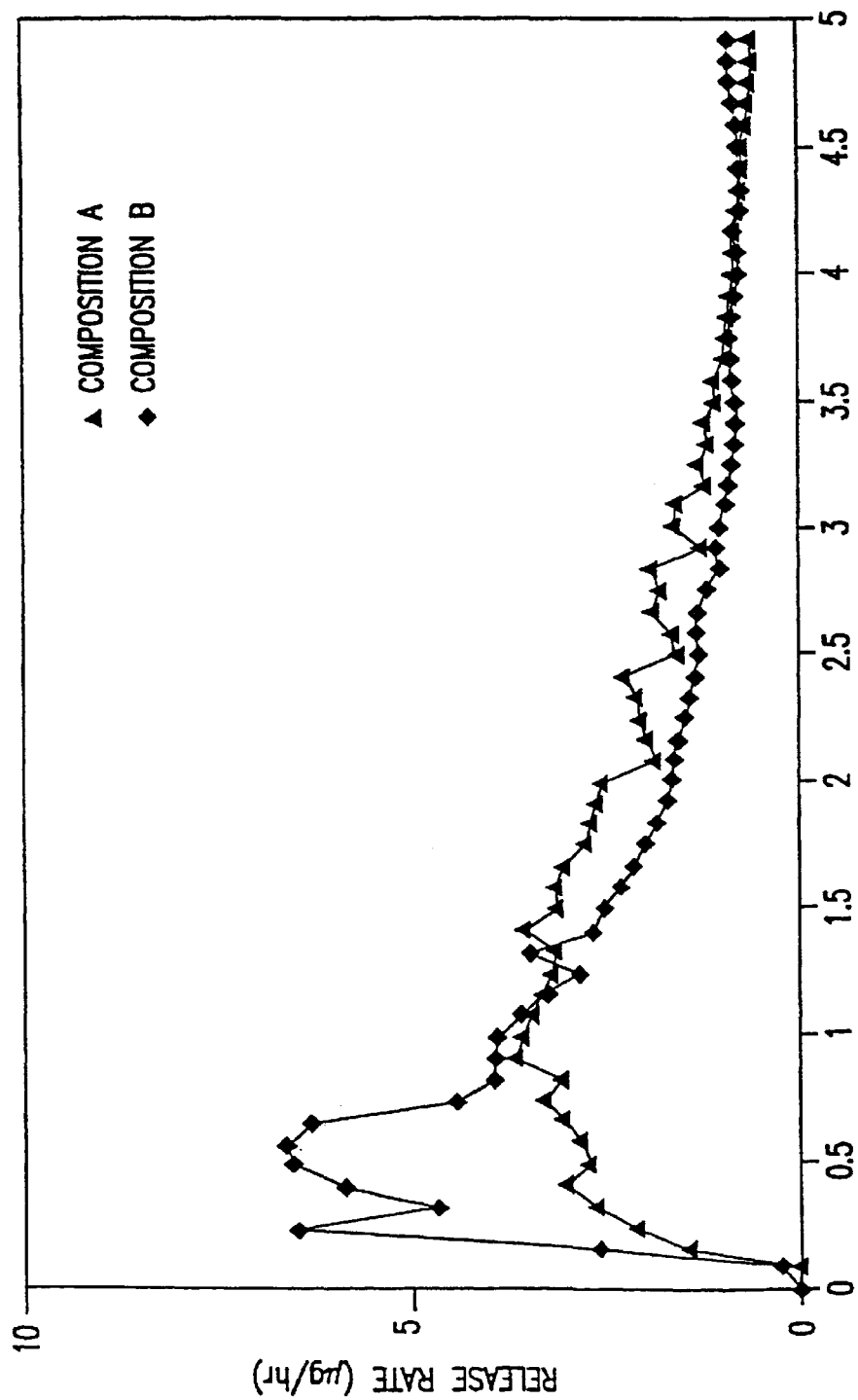
FIG. 1 shows the illustrious results of Example 21 regarding release rate curves for an inventive and a comparative ophthalmic composition.

The present inventors have discovered that by providing the non-steroidal anti-inflammatory (NSAI) agent as a solid and in the presence of a divalent cation, the dissolution of the NSAI agent during the first several minutes at neutral pH is sufficiently slowed so as to further avoid stinging the eye. For reasons that are not entirely clear, stinging and burning irritation are typically only induced during the first minutes after contact with a sufficiently high concentration of NSAI agent. After this initial time period, the eye is apparently no longer sensitive to the NSAI agent, regardless of its concentration level. Thus, by delaying the dissolution of the NSAI agent during the first few minutes, the initial NSAI agent concentration on the eye can be sufficiently low to avoid irritation. Afterward, the high concentration caused by the dissolution of the solid NSAI agent precipitate is too late to cause irritation. In this way the stinging problem is effectively avoided while still providing a topically effective dose of NSAI agent.

In contrast, the typical prior art composition would supply all of the NSAI agent as a solute and thus apply an immediate high concentration to the surface of the eye. Such a technique has the greatest chance of inducing stinging in the patient. While the use of sodium diclofenac in both suspension and solution form, simultaneously, is described in the above-mentioned co-pending application and provides good results, the presence of a divalent cation in accordance with the present invention improves the avoidance of stinging. The divalent cation reduces the solubility of the NSAI agent in the aqueous medium and thus reduces the dissolution rate of the solid NSAI agent precipitate during the first several minutes after administration.

As used in this application, the term "divalent cation" means a cation having a +2 charge. The divalent cation can be in either solid or dissolved form, or both. In solid form, the cation is ionically bonded to an anion thereby making a salt. When in solution, the cation is not required to be directly associated with a specific anion. Typically the cation is, or contains, a metal; i.e., a "metal divalent cation". Examples of suitable divalent cations include Group IIA elements (alkaline earth metals) such as calcium, magnesium, barium, etc. Particularly preferred divalent cations are $Ca^{++}$ and $Mg^{++}$. The divalent cation and any salts thereof in the composition are pharmacologically acceptable so as to not harm the eye or the patient. Typical anions include chlorides, sulfates, and the NSAI agent.

The divalent cation is only required to be present in the composition and is not necessarily associated or otherwise bonded with the NSAI agent. In one embodiment, all or essentially all of the divalent cation is in solution with no cation present in the solid NSAI agent.

The amount of divalent cation is at least about 0.5 equivalents and generally within the range of from about 0.5 to about 10 equivalents, more preferably 1.0 to about 5.0 equivalents, per mole of NSAI. Note that molar equivalents are specified since NSAI agents may be monovalent and hence stoichiometrically require only half as many moles of the divalent cation. Thus, for example, one mole of $Mg^{++}$ per one mole of diclofenac anion would be 2.0 equivalents of $Mg^{++}$ (twice as much cation as is required).

"Non-steroidal anti-inflammatory agents" as used herein are intended to mean any non-narcotic analgesic/non-steroidal anti-inflammatory compound useful in treating or ameliorating a disease or medical condition. They include drugs intended to therapeutically treat conditions of the eye itself or the tissue surrounding the eye and drugs administered via the ophthalmic route to treat therapeutically a local condition other than that involving the eye. Preferably the NSAI agent is useful as a cyclooxygenase inhibitor. Cyclooxygenase is essential in the biosynthesis of prostaglandins which have been shown in many animal models to be mediators of intraocular inflammation. The NSAI agent typically contains at least one carboxy group in its molecule.

Examples of NSAI agents that are useful in the present invention include aspirin, benoxaprofen, benzofenac, bucloxic acid, butibufen, caiprofen, cicloprofen, cinmetacin, clidanac, clopirac, diclofenac, etodolac, fenbufen, fenclofenac, fenclorac, fenoprofen, fentiazac, flunoxaprofen, furaprofen, flurbiprofen, furobufen, furofenac, ibuprofen, ibufenac, indomethacin, indoprofen, isoxepac, ketorolac, ketroprofen, lactorolac, lonazolac, metiazinic, miroprofen, naproxen, oxaprozin, oxepinac, phenacetin, pirprofen, pirazolac, protizinic acid, sulindac, suprofen, tiaprofenic acid, tolmetin, and zomepirac. Preferably, the NSAI agent is selected from the group consisting of diclofenac, suprofen, flurbiprofen and mixtures thereof.

The composition of the present invention contains at least 80% of the NSAI agent in precipitate form. This means that 80%, by mole, of the NSAI is in a solid state. The remainder, if any, is in solution. In this regard the term "precipitate" is not meant to require that the solid was formed by a precipitation process, although such is usually the case. Preferably, 85% to 95% of the NSAI agent is in precipitate form. The precipitate is usually dispersed in the aqueous medium or carried on a dispersed carrier such as a polymer particle, but such a dispersed form is not required.

In one embodiment of the invention, the precipitate is the free-acid form (or free-base form) and not a salt form of the NSAI agent. Generally, the free-acid is almost always formed, even if formed from an NSAI divalent salt solution. For example, originally, a calcium or magnesium salt of diclofenac was believed to have been formed as the precipitate. However, subsequent investigations showed that the precipitate was in fact the free-acid of diclofenac. The divalent cation remained in solution. The presence of this divalent cation serves to reduce the solubility of the NSAI agent; thereby causing the desired delayed release. Alternatively, the precipitate can be a salt of the divalent cation and the NSAI agent or a mixture of salt and the free-acid forms.

The remaining portion, if any, of the NSAI agent is in solution (a solute) and is typically in a salt form such as sodium diclofenac or magnesium diclofenac for example.

The total amount of NSAI agent present in the composition is an amount effective to treat the selected target condition. Generally the concentration will be about 0.001 to about 5.0% by weight of the composition. Preferably, the drug is about 0.005 to about 3.0% by weight of the composition, and more preferably about 0.1 to about 1.0% by weight of the composition. These same ranges of drug concentrations are believed to be appropriate for treating a wide range of conditions, such as those discussed above, in addition to treating inflammation.

The pH of the aqueous medium is set to be within the range of 4.0 to 6.7. Importantly the pH is below that of the pH of the eye. In this way, upon topical application of the composition to the eye, an increase in pH occurs thereby changing the solubility equilibrium of the NSAI agent and causing the precipitate to dissolve. As slow dissolution during the first minutes after administration is desired, the use of a lower pH is preferred, such as from 4.0 to 6.5.

The most preferred composition contains solid diclofenac in free-acid form and all of the divalent cation as well as the remaining diclofenac in solution. The divalent cation is preferably calcium or magnesium. One of the advantages of this composition is the ability to fully (100%) redissolve at pH 7.0 or above with adequate residence time in the eye. This means that all of the diclofenac is recovered and made bioavailable when the composition is placed into the eye.

The aqueous medium used in the present invention is made of water that has no physiologically or ophthalmologically harmful constituents. Typically purified or deionized water is used. The pH is adjusted by adding any physiologically and ophthalmologically acceptable pH adjusting acids, bases or buffers. Examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, THAM (trishydroxymethylamino-methane), and the like. Salts and buffers would include citrate/dextrose, sodium bicarbonate, ammonium chloride and mixtures of the aforementioned acids and bases.

The osmotic pressure ($\pi$) of the present composition is preferably from about 10 milliosmolar (mOsM) to about 400 mOsM. If necessary, the osmotic pressure can be adjusted by using appropriate amounts of physiologically and ophthalmologically acceptable salts or excipients. When needed, sodium chloride is preferred to approximate physiologic fluid, and amounts of sodium chloride ranging from about 0.01% to about 1% by weight, and preferably from about 0.05% to about 0.45% by weight, based on the total weight of the composition, are typically used. Equivalent amounts of one or more salts made up of cations such as potassium, ammonium and the like and anions such as chloride, citrate, ascorbate, borate, phosphate, bicarbonate, sulfate, thiosulfate, bisulfate, sodium bisulfate, ammonium sulfate, and the like can also be used in addition to or instead of sodium chloride to achieve osmolalities within the above-stated range. Sugars like mannitol, dextrose, glucose or other polyols may be added to adjust osmolarity.

The composition of the present invention may contain water soluble polymers or water insoluble polymers as a suspending agent. Examples of such soluble polymers are dextran, polyethylene glycols, polyvinylpyrolidone, polysaccaride gels, Gelrite®, and cellulosic polymers like hydroxypropyl methylcellulose as well as other polymeric demulcents. Water insoluble polymers are preferably crosslinked carboxy-vinyl polymers.

A preferred embodiment of the invention provides the ophthalmic composition as either gel or liquid drops that contain water insoluble, water-swellable polymers which release the drug over time; i.e., over one or more hours. Preferably, the polymer is contained in an amount of about 0.1 to about 6.5%, more preferably about 0.5 to about 1.3% by weight based on the total weight of the composition. These polymer carriers include lightly crosslinked carboxy-containing polymers (such as polycarbophil (Noveon AA-1) or Carbopol®) which typically have an average dry particle size of not more than about 50 $\mu$m in equivalent spherical diameter, more preferably not more than 20$\mu$m in equivalent spherical diameter. The crosslinked carboxy-containing polymers can be formed from carboxy-containing monoethylenically unsaturated monomers such as acrylic acid, methacrylic acid, crotonic acid, and the like and from suitable crosslinking agents such as difunctional crosslinkers including divinyl glycol, divinyl benzene, 2,5-dimethyl-1,5-hexadiene, and polyalkenyl polyether compounds. The carboxy-containing polymer backbone can be a homopolymer or a copolymer comprised of two or more monomer species. When two or more monomers are used, non-carboxy-containing monomers may be employed, such as acrylic acid esters and methacrylic acid esters (ethyl acrylate, methyl methacrylate, etc.), vinyl acetate, N-vinylpyrrolidone, and the like. These non-carboxy-containing comonomers are preferably present in an amount of not more than 40 wt. %, more preferably 0 to 20 wt. %, based on the total weight of monomers present. The amount of crosslinker employed is preferably from about 0.01 to 5%, more preferably from 0.1 to 1.0%, based on the total weight of monomers present. Suitable carboxy-containing polymers for use in the present invention and methods for making them are described in U.S. Pat. No. 5,192,535 to Davis et al. which is hereby incorporated by reference. A suitable carboxy-containing polymer system for use in the present composition is known by the tradename DuraSite®, containing polycarbophil, which is a sustained release topical ophthalmic delivery system that releases the drug at a controlled rate.

The ophthalmic compositions of the present invention have a viscosity that is suited for the selected route of administration. A viscosity up to about 30,000 centipoise is useful for a drop. About 30,000 to about 100,000 centipoise is an advantageous viscosity range for ophthalmic administration in ribbon form. The viscosity can be controlled in many ways known to the worker skilled in the art.

In one embodiment, the amount of insoluble lightly crosslinked polymer particles, the pH, and the osmotic pressure can be correlated with each other and with the degree of crosslinking to give a composition having a viscosity in the range of from about 500 to about 100,000 centipoise, and preferably from about 1,000 to about 30,000 or about 1,000 to about 10,000 centipoise, as measured at room temperature (about 25° C.) using a Brookfield Digital LVT Viscometer equipped with a number 25 spindle and a 13R small sample adapter at 12 rpm. Alternatively, when water soluble polymers are used, such as hydroxypropyl methylcellulose, the viscosity will typically be about 10 to about 400 centipoise, more typically about 10 to about 200 centipoises or about 10 to about 25 centipoise.

Ophthalmic compositions of the present invention may be formulated so that they retain the same or substantially the same viscosity in the eye that they had prior to administration to the eye. Alternatively, ophthalmic compositions of the present invention may be formulated so that there is increased gelation upon contact with tear fluid. For instance, when a formulation containing DuraSite® is administered to the eye at a lower pH, the DuraSite® system swells upon contact with tears. This gelation or increase in gelation leads to entrapment of the suspended drug particles, thereby extending the residence time of the composition in the eye. The drug is released slowly as the suspended particles dissolve over time as the solubility of the drug is higher in the tear fluid. All these events eventually lead to increased patient comfort, increase in the time the drug is in contact with the eye tissues, thereby increasing the extent of drug absorption and duration of action of the formulation in the eye.

The viscous gels that result from fluid eye drops typically have residence times in the eye ranging from about 2 to about 12 hours, e.g., from about 3 to about 6 hours. The agents contained in these drug delivery systems will be released from the gels at rates that depend on such factors as the drug itself and its physical form, the extent of drug loading and the pH of the system, as well as on any drug delivery adjuvants, such as ion exchange resins compatible with the ocular surface, which may also be present. Preferably, the compositions provide a sustained concentration of the NSAI agent of between $10^{-8}$ and $10^{-4}$ M, and more preferably between $10^{-7}$ and $10^{-5}$ M, in the aqueous or treated tissue of the eye for at least two hours, preferably at least three hours.

The composition of the present invention will ordinarily contain surfactants and, if desired, adjuvants, including additional medicaments, buffers, antioxidants, tonicity adjusters, preservatives, thickeners or viscosity modifiers, and the like. Additives in the formulation may desirably include sodium chloride, EDTA (disodium edetate), phosphonic acid, BAK (benzalkonium chloride), perborate salt, sorbic acid, methyl paraben, propyl paraben, and/or chlorhexidine. It should be noted that BAK was found to be unexpectedly compatible with diclofenac in the present ophthalmic composition. While the reasons for this are not entirely clear, and without wishing to be bound by any theory, the presence of the divalent cation is believed to prevent the BAK from complexing the diclofenac out of the system.

The preferred preservative in the divalent cation nonsteroidal anti-inflammatory ophthalmic composition is sodium perborate in an amount of from about 0.01 to 0.5 wt. %, more preferably from 0.03 to 0.3 wt. %.

In this connection, applicants have also discovered that a perborate salt can be effectively stabilized by the presence of both a polyphosphonic acid peroxy stabilizer and EDTA. This discovery was surprising in that the presence of EDTA would have been expected to interfere with the complexing action of the polyphosphonic acid stabilizer. Moreover, the presence of EDTA surprisingly enhances the stability of the composition. This three component preservative system is applicable to any aqueous ophthalmic composition including saline solutions, eye lubricants, medicated compositions, etc. and is not limited to use in combination with a non-steroidal anti-inflammatory agent. The preservative system comprises (1) about 0.01 to 0.5 wt. %, preferably 0.03 to 0.3 wt. %, of a perborate salt; (2) about 0.001 to 0.06 wt. %, preferably 0.003 to 0.03 wt. %, of a polyphosphonic acid peroxy stabilizer; and (3) about 0.01 to 0.1 wt. % of EDTA, based on the total weight of the composition. The preservative system may additionally comprise 0.05 to 0.2 parts of BAK. The perborate salt is preferably sodium perborate.

A "polyphosphonic acid peroxy stabilizer" means any compound containing at least two $-PO_3H_2$ moieties or the pharmacologically acceptable salt thereof, and that is capable of stabilizing a peroxy compound. Such compounds are generally well known in the prior art. Preferably the polyphosphonic acid peroxy stabilizer is a compound of the formula I or II or a pharmacologically acceptable salt thereof:

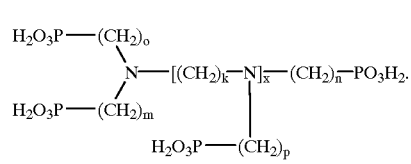

wherein x is an integer of 0 to 3 and k, m, n, o, and p are each independently an integer of 1 to 4. Preferably x is 2 and k, m, n, o, and p are each 1 or 2.

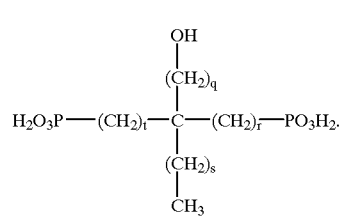

wherein q, r, s, and t are each independently an integer of 0 to 4. Preferably q, r, s, and t are 0 or 1, and most preferably all are zero.

Many of the compounds of formulas I and II are sold by Monsanto under the DEQUEST brand name. A preferred compound is diethylene triamine penta(methylenephosphonic acid), which corresponds to formula I, and is sold as DEQUEST 2060.

The water used in the preserved ophthalmic composition of the present invention is normally sterilized. The preserved ophthalmic composition can contain additional ingredients including any of the ingredients discussed previously. For example, sodium chloride can be present as part of a saline solution; a carboxy-containing polymer, such as polycarbophil, can be present to form a stably preserved suspension; etc. With respect to the latter composition, a preferred form further includes magnesium ions ($Mg^{++}$) in addition to the polymer and the perborate/polyphosphonic acid peroxy stabilizer/EDTA system. The amount of magnesium is not particularly limited, but typically ranges from about 0.005 to 0.5wt. %, preferably 0.02 to 0.2 wt. % (the amount of polymer being the same as described above). Such a composition is well preserved and also exhibits a stable viscosity during storage.

Alternatively, a pharmaceutically active agent may be present as part of a medicated composition. In this regard, a "pharmaceutically active agent" is broader in scope than an NSAI agent and embraces any agent with pharmaceutical utility that can be used to treat the eye or administered via the eye in treating a disease or condition of the patient.

The preservative system can used in a variety of aqueous ophthalmic compositions such as saline solutions for cleaning contact lenses, as an eye wash, as an eye lubricating or wetting composition, and as a medicated composition. The preservative system of the present invention is preferably combined with the above-described divalent cation-containing ophthalmic composition.

The compositions of the present invention can be prepared from known materials through the application of known techniques by workers of ordinary skill in the art without undue experimentation. In general, compositions are formed by combining the NSAI agent, a divalent cation source, optionally a polymer, and water. In one embodiment, the divalent cation is first completely dissolved in an aqueous solution, adjusting the pH or temperature if necessary. The divalent cation source is typically in the form of a salt, but any water soluble form is acceptable. Preferred divalent cation sources are divalent metal salts such as $CaCl_2$, $MgCl_2$ and $MgSO_4$. The NSAI agent is then added, typically in the form of a salt although such is not required, resulting in precipitation of the NSAI agent. Generally the precipitation will be immediate without adjustment of the solution. However, aids in causing precipitation, such as seeding, may also be used, either alone, or in addition to pH modifiers, in order to encourage or enhance precipitate formation.

After the precipitation of the NSAI agent, the polymer, if any, can be added to the aqueous composition by conventional techniques. The resulting composition is sterilized and then the remaining ingredients such as buffers, surfactants, etc. are added thereto. It is not preferred to heat sterilize after the precipitate is formed in that redissolving and recrystallization of the precipitate can occur and may adversely effect the precipitate, e.g. increasing the crystal size. Alternatively, the precipitate-containing solution can be combined with a sterilized aqueous polymer dispersion, optionally containing buffer, surfactant, preservative and/or other ingredients.

In another embodiment, the NSAI agent is added to a solution that contains the divalent cation source and optionally a dispersed polymer to form the precipitate-containing composition. The solution can be previously sterilized and preferably contains all ingredients except the NSAI agent (and possibly a final portion of water) at the time of NSAI agent addition.

If a carboxy-containing polymer is to be added to the composition, then the amount of free divalent cation added should be controlled so as not to significantly exceed the stoichiometric amount. Specifically, a large excess of free calcium, magnesium, divalent cations, etc., could react with and complex the polymer thereby disrupting the suspension and preventing the release of the NSAI agent. Alternatively a chelating agent such as EDTA should be provided in the composition in order to chelate any excess divalent cation (e.g., calcium, magnesium, etc.). Such a chelating agent can be provided in the dispersed polymer-containing solution, if desired. The amount of chelating agent depends in part on the amount of NSAI agent and divalent cation source and need only be sufficient to avoid the above-mentioned disruption.

Although the above described methods are suitable for making the present ophthalmic composition, they are not the only methods. Other methods for making the present composition can be used.

The ophthalmic compositions according to the present invention can be topically administered in accordance with techniques familiar to persons skilled in the art. The finished formulations are preferably stored prior to use in opaque or brown containers to protect them from light exposure, and under an inert atmosphere. These compositions can be packaged in preservative-free, single-dose non-reclosable containers. This permits a single dose of the medicament to be delivered to the eye as a drop or ribbon, with the container then being discarded after use. Such containers eliminate the potential for preservative-related irritation and sensitization of the corneal epithelium, as has been observed to occur particularly from ophthalmic medicaments containing mercurial preservatives. Multiple dose containers can also be used, if desired, particularly since relatively low viscosities can be obtained in compositions of the invention which permit constant, accurate dosages to be administered drop-wise to the eye as many times each day as necessary.

The following non-limiting example serves to illustrate certain features of the present invention.

EXAMPLES 1–5

Hydrated polymer is prepared by adding 2.3 grams of polycarbophil or 2.4 grams of Carbopol®974P to 100 grams of purified water in a 600 ml beaker and mixing for 30 minutes with an overhead stirrer. Then, 0.2 gram of edetate disodium is added and mixed for 5 minutes followed by 1 gram of sodium chloride, which is also mixed for 5 minutes. In a separate 50 ml beaker, different amounts of poloxamer 407 is dissolved in 15 grams of purified water. The solution is then added to the polycarbophil or Carbopol dispersion and mixed for 5 minutes. After adjusting the pH of the dispersion to 4 using 2N sodium hydroxide, it is sterilized by autoclaving at 121° C. for 20 minutes. The drug solution is prepared by combining, in a separate 100 ml beaker, different amounts of diclofenac sodium, 2 grams of mannitol and various amounts of $CaCl_2$ dihydrate in 40 grams of purified water. The resulting suspension is then added to the polycarbophil or Carbopol dispersion and mixed for 15 minutes. The formulation is neutralized by adjusting the pH of the formulation to 6.0 using 2N sodium hydroxide. This causes it to gel. Finally, the weight of the solution is brought to 200 grams by adding purified water.

TABLE 1

Amount Of Each Component Added to make the Formulations of Examples 1–4

| Ingredients | Example 1 Wt. % | Example 2 Wt. % | Example 3 Wt. % | Example 4 Wt. % |
| --- | --- | --- | --- | --- |
| polycarbophil | 1.15 | 1.15 | 1.15 | 1.15 |
| edetate disodium | 0.1 | 0.1 | 0.1 | 0.1 |
| sodium chloride | 0.5 | 0.5 | 0.5 | 0.5 |
| diclofenac sodium | 0.1 | 0.3 | 0.1 | 0.3 |
| calcium chloride dihydrate | 0.0173 | 0.0519 | 0.0208 | 0.0623 |
| poloxamer 407 | 0.05 | 0.1 | 0.05 | 0.1 |
| mannitol | 1.0 | 1.0 | 1.0 | 1.0 |
| purified water q.s. | 100 | 100 | 100 | 100 |

Amount of Each Component Added to make the Formulation of Example 5

| Ingredients | Example 5 Wt. % |
| --- | --- |
| Carbopol ® 974P | 1.2 |
| edetate disodium | 0.1 |

TABLE 1-continued

| | |
|---|---|
| sodium chloride | 0.5 |
| diclofenac sodium | 0.1 |
| calcium chloride dihydrate | 0.0173 |
| poloxamer 407 | 0.05 |
| mannitol | 1.0 |
| purified water q.s. | 100 |

EXAMPLES 6–9

Hydrated polycarbophil (Noveon AA-1) is prepared by adding 2.3 grams of polycarbophil to 100 grams of purified water in a 600 ml beaker and mixing for 30 minutes with an overhead stirrer. Then 0.2 gram of edetate disodium is added and mixed for 5 minutes followed by 1 gram of sodium chloride mixed for 5 minutes. In a separate 50 ml beaker, different amounts of poloxamer 407 (a commercially available surfactant) is dissolved in 15 grams of purified water. The solution is then added to polycarbophil dispersion and mixed for 5 minutes. After adjusting the pH of the dispersion to 4 using 2N sodium hydroxide, it is sterilized by autoclaving at 121° C. for 20 minutes. The drug solution is prepared by combining, in a separate 100 ml beaker, different amounts of diclofenac sodium, 2 grams of mannitol and various amounts of magnesium sulfate heptahydrate in 40 grams of purified water. The resulting suspension is then added to the polycarbophil dispersion and mixed for minutes. The formulation is neutralized by adjusting the pH of the formulation to 6.0 using 2N sodium hydroxide. This causes it to gel. Finally, the weight of the solution is brought to 200 grams by adding purified water. The amount of each component in Examples 6–9 is listed in Table 2.

TABLE 2

Amount Of Each Component Added to Make the Formulations of Examples 6–9

| Ingredients | Example 6 Wt. % | Example 7 Wt. % | Example 8 Wt. % | Example 9 Wt. % |
|---|---|---|---|---|
| polycarbophil | 1.15 | 1.15 | 1.15 | 1.15 |
| edetate disodium | 0.1 | 0.1 | 0.1 | 0.1 |
| sodium chloride | 0.5 | 0.5 | 0.5 | 0.5 |
| diclofenac sodium | 0.1 | 0.3 | 0.1 | 0.3 |
| magnesium sulfate heptahydrate | 0.0387 | 0.116 | 0.0464 | 0.139 |
| poloxamer 407 | 0.05 | 0.1 | 0.05 | 0.1 |
| mannitol | 1.0 | 1.0 | 1.0 | 1.0 |
| purified water q.s. | 100 | 100 | 100 | 100 |

EXAMPLES 10–13

Hydrated polycarbophil (Noveon AA-1) is prepared by adding 1.6 grams of polycarbophil to 100 grams of purified water in a 600 ml beaker and mixing for 30 minutes with an overhead stirrer. Then 0.2 gram of edetate disodium is added and mixed for 5 minutes followed by 0.5 grams of sodium chloride mixed for 5 minutes. In a separate 50 ml beaker, 0.02 grams of benzalkonium chloride is dissolved in 20 grams of purified water. The solution is then added to the polycarbophil dispersion and mixed for 5 minutes. In a separate 50 ml beaker, different amounts of poloxamer 407 is dissolved in 15 grams of purified water. The solution is then added to polycarbophil dispersion and mixed for 5 minutes. After adjusting the pH of the dispersion to 4 using 2N sodium hydroxide, it is sterilized by autoclaving at 121° C. for 20 minutes. The drug solution is prepared by combining, in a separate 100 ml beaker, different amounts of diclofenac sodium, 3.0 grams of sorbitol, 0.4 grams of glycerin and various amounts of calcium chloride dihydrate in 40 grams of purified water. The resulting suspension is then added to the polycarbophil dispersion and mixed for 15 minutes. The formulation is neutralized by adjusting the pH of the formulation to 6.0 using 2N sodium hydroxide. This causes it to gel. Finally, the weight of the solution is brought to 200 grams by adding purified water. The amount of each component in Examples 10–13 is listed in Table 3.

TABLE 3

Amount Of Each Component Added to Make the Formulations in Examples 10–13

| Ingredients | Example 10 Wt. % | Example 11 Wt. % | Example 12 Wt. % | Example 13 Wt. % |
|---|---|---|---|---|
| polycarbophil | 0.8 | 0.8 | 0.8 | 0.8 |
| edetate disodium | 0.1 | 0.3 | 0.1 | 0.1 |
| sodium chloride | 0.25 | 0.25 | 0.25 | 0.25 |
| diclofenac sodium | 0.1 | 0.3 | 0.1 | 0.3 |
| calcium chloride dihydrate | 0.0173 | 0.0519 | 0.0208 | 0.0623 |
| benzalkonium chloride | 0.01 | 0.01 | 0.01 | 0.01 |
| poloxamer 407 | 0.05 | 0.1 | 0.05 | 0.1 |
| glycerin | 0.2 | 0.2 | 0.2 | 0.2 |
| sorbitol | 1.5 | 1.5 | 1.5 | 1.5 |
| purified water q.s. | 100 | 100 | 100 | 100 |

EXAMPLES 14–17

Hydrated polycarbophil (Noveon AA-1) is prepared by adding 1.6 , grams of polycarbophil to 100 grams of purified water in a 600 ml beaker and mixing for 30 minutes with an overhead stirrer. Then 0.2 gram of edetate disodium is added and mixed for 5 minutes followed by 0.5 grams of sodium chloride mixed for 5 minutes. In a separate 50 ml beaker, 0.02 grams of benzalkonium chloride is dissolved in 20 grams of purified water. The solution is then added to the polycarbophil dispersion and mixed for 5 minutes. In a separate 50 ml beaker, different amounts of poloxamer 407 is dissolved in 15 grams of purified water. The solution is then added to polycarbophil dispersion and mixed for 5 minutes. After adjusting the pH of the dispersion to 4 using 2N sodium hydroxide, it is sterilized by autoclaving at 121° C. for 20 minutes. The drug solution is prepared by combining, in a separate 100 ml beaker, different amounts of diclofenac sodium, 3.0 grams of sorbitol, 0.4 grams of glycerin and various amounts of magnesium sulfate heptahydrate in 40 grams of purified water. The resulting suspension is then added to the polycarbophil dispersion and mixed for 15 minutes. The formulation is neutralized by adjusting the pH of the formulation to 6.0 using 2N sodium hydroxide. This causes it to gel. Finally, the weight of the solution is brought to 200 grams by adding purified water. The amount of each component in Examples 14–17 is listed in Table 4.

TABLE 4

Amount Of Each Component Added to Make the Formulations of Examples 14–17

| Ingredients | Example 14 Wt. % | Example 15 Wt. % | Example 16 Wt. % | Example 17 Wt. % |
|---|---|---|---|---|
| polycarbophil (Noveon AA-1) | 0.8 | 0.8 | 0.8 | 0.8 |
| edetate disodium | 0.1 | 0.3 | 0.1 | 0.1 |
| sodium chloride | 0.25 | 0.25 | 0.25 | 0.25 |
| diclofenac sodium | 0.1 | 0.3 | 0.1 | 0.3 |
| magnesium sulfate heptahydrate | 0.0387 | 0.116 | 0.0464 | 0.139 |
| benzalkonium chloride | 0.01 | 0.01 | 0.01 | 0.01 |
| poloxamer 407 | 0.05 | 0.1 | 0.05 | 0.1 |
| glycerin | 0.2 | 0.2 | 0.2 | 0.2 |
| sorbitol | 1.5 | 1.5 | 1.5 | 1.5 |
| purified water q.s. | 100 | 100 | 100 | 100 |

EXAMPLES 18–19

Hydrated polycarbophil (Noveon AA-1) is prepared by adding 1.6 grams of polycarbophil to 100 grams of purified water in a 600 ml beaker and mixing for 30 minutes with an overhead stirrer. Then 0.2 gram of edetate disodium is added and mixed for 5 minutes followed by 1 grams of sodium chloride mixed for 5 minutes. In a separate 50 ml beaker, 0.02 grams of benzalkonium chloride is dissolved in 20 grams of purified water. The solution is then added to the polycarbophil dispersion and mixed for 5 minutes. In a separate 50 ml beaker, different amounts of poloxamer 407 is dissolved in 15 grams of purified water. The solution is then added to polycarbophil dispersion and mixed for 5 minutes. After adjusting the pH of the dispersion to 4 using 2N sodium hydroxide, it is sterilized by autoclaving at 121° C. for 20 minutes. The drug solution is prepared by combining, in a separate 100 ml beaker containing 40 grams of purified water, Suprofen or Flurbiprofen sodium, 3.0 grams of sorbitol, 0.4 grams of glycerin and an amount of either magnesium sulfate heptahydrate or calcium chloride dihydrate sufficient to form a precipitate of the drug. The resulting suspension is then added to the polycarbophil dispersion and mixed for 15 minutes. The formulation is neutralized by adjusting the pH of the formulation to 6.0 using 2N sodium hydroxide. This causes it to gel. Finally, the weight of the solution is brought to 200 grams by adding purified water.

EXAMPLE 20

Hydrated hydroxypropyl methyl cellulose (HPMC) is prepared by adding 2.0 grams of HPMC to 100 grams of purified water in a 600 ml breaker and mixing for 4 hours with an overhead stirrer. Then, 1 gram of sodium chloride, 0.242 grams of dibasic sodium phosphate and 0.055 grams of monobasic sodium phosphate are added and mixed for 5 minutes. In a separate 50 ml beaker, 0.02 grams of benzalkonium chloride is dissolved in 20 grams of purified water. The solution is then added to the HPMC dispersion and mixed for 5 minutes. In a separate 50 ml beaker, different amounts of poloxamer 407 is dissolved in 15 grams of purified water. The solution is then added to the HPMC dispersion and mixed for 5 minutes. It is sterilized by autoclaving at 121° C. for 20 minutes. The drug solution is prepared by combining, in a separate 100 ml beaker containing 40 grams of purified water, either Diclofenac sodium, Suprofen or Flurbiprofen sodium with 3.0 grams of sorbitol, 0.4 grams of glycerin and an amount of either magnesium sulfate heptahydrate or calcium chloride dihydrate sufficient to form a precipitate of the drug. The resulting suspension is then added to the HPMC dispersion and mixed for 15 minutes. The formulation is neutralized by adjusting the pH of the formulation to 6.0 using 2N sodium hydroxide. Finally, the weight of the solution is brought to 200 grams by adding purified water.

EXAMPLE 21

To demonstrate the surprising effect of the present invention, two ophthalmic compositions are prepared, which essentially differ from each other with respect to the presence or absence of a divalent cation. Composition A, made in accordance with the present invention, includes the presence of a divalent cation ($Mg^{++}$). Comparative Composition B does not have a divalent cation, but does have a monovalent cation ($Na^+$) and is similar to the exemplified compositions set forth in the above-mentioned co-pending application Ser. No. 08/248,500, filed May 24, 1994. The compositions are prepared from the ingredients listed in the table below.

| Ingredient | Composition A (wt. %) | Composition B (wt. %) |
|---|---|---|
| Diclofenac sodium | 0.033 | 0.033 |
| Magnesium chloride | 0.2 | — |
| Sodium chloride | — | 0.5 |
| Sodium perborate | 0.28 | — |
| Polycarbophil | 0.7 | 1.15 |
| Phosphonic acid (Dequest 2060) | 0.006 | — |
| EDTA | — | 0.1 |
| Mannitol | 1.5 | 1.0 |
| Boric acid | 0.75 | — |
| Poloxamer 407 | 0.05 | 0.05 |
| Sodium hydroxide | q.s. to pH 6.1 | q.s. to pH 6.0 |
| Purified water | q.s. to 100 | q.s. to 100 |

Each composition is tested to determine its release rate over time. Samples are placed into a buffer solution contained in a cell. The cell size is 0.6 ml and the buffer is a phosphonate buffered saline solution containing 0.9% NaCl and 10 mM phosphate at pH 7.4. Additional buffer is then steadily passed through the cell via a peristalic pump at an appropriate rate to model natural liquid turnover in the eye; here 6 ml/hr. The temperature is maintained at approximately 37° C. (body temperature). The concentration of the medicament in the eluted buffer is measured over time by spectroscopy, to thereby form a release rate curve. Illustrious results are depicted in FIG. 1.

The release rate curve shown for composition A according to the present invention shows a delay in the initial release. In contrast, the release rate curve shown for composition B displays a higher peak during the initial release. Thus, the composition according to the present invention provides for improved delayed release during the important initial contact period with the eye and thereby reduces the tendency of stinging.

EXAMPLE 22

Further embodiments of the present invention are obtained by combining the ingredients set forth in the following table.

| Ingredient | Composition 22A (wt. %) | Composition 22B (wt. %) |
|---|---|---|
| Sodium diclofenac | 0.03 to 0.1 | 0.03 to 0.1 |
| Magnesium chloride hexahydrate | 0.02 to 0.2 | 0.02 to 0.2 |
| Sodium perborate | 0.28 | 0.28 |
| BAK | — | 0.01 |
| Polycarbophil | 0.825 | 0.825 |
| Dequest 2060 | 0.006 | 0.006 |
| EDTA | 0.025 | 0.025 |
| Mannitol | 1.5 | 1.5 |
| Sodium chloride | 0.05 | 0.05 |
| Boric acid | 1.0 | 1.0 |
| Poloxamer 407 | 0.05 | 0.05 |
| Sodium hydroxide | q.s. to pH 6.1 | q.s. to pH 6.1 |
| Purified water | q.s. to 100 | q.s. to 100 |

The ingredients, except for the sodium diclofenac, are preferably combined so as to form a polymer suspension. Then the sodium diclofenac is added resulting in the precipitation of the diclofenac free-acid. A final portion of water is then added to complete the composition.

The above discussion of this invention is directed primarily to preferred embodiments and practices thereof. It will be readily apparent to those skilled in the art that further changes and modifications in actual implementation of the concepts described herein can easily be made or may be learned by practice of the invention, without departing from the spirit and scope of the invention as defined by the following claims.

We claim:

1. An ophthalmic composition comprising an aqueous medium containing an effective amount of a non-steroidal anti-inflammatory agent, wherein from about 80 mol. % to less than 100 mol. % of said agent is in the form of a precipitate, and at least about 0.5 mole equivalents of a pharmacologically acceptable divalent cation per mole of said non-steroidal anti-inflammatory agent precipitate, said aqueous medium having a pH in the range of from 4.0 to 6.7.

2. The composition according to claim 1, wherein said non-steroidal anti-inflammatory agent is selected from the group consisting of diclofenac, suprofen, and flurbiprofen.

3. The composition according to claim 2, wherein said non-steroidal anti-inflammatory agent is diclofenac.

4. The composition according to claim 1, wherein said pharmacologically acceptable divalent cation is a Group IIA metal.

5. The composition according to claim 4, wherein said Group IIA divalent metal cation is calcium or magnesium.

6. The composition according to claim 1, wherein said precipitate is in a free-acid form.

7. The composition according to claim 6, wherein said divalent cation is present as a solute in said aqueous medium.

8. The composition according to claim 7, wherein said divalent cation is present from 1 to 5 times the stoichiometric amount equivalent to the molar amount of said non-steroidal anti-inflammatory agent precipitate.

9. The composition according to claim 8, wherein 85 to 95% of said non-steroidal anti-inflammatory agent is in said precipitate form.

10. The composition according to claim 9, wherein said NSAI agent is diclofenac and said divalent cation is $Mg^{++}$.

11. The composition according to claim 1, further comprising a polymer.

12. The composition according to claim 11, wherein said polymer is water insoluble and water swellable.

13. The composition according to claim 12, wherein said polymer is a crosslinked carboxy-containing polymer.

14. The composition according to claim 13, wherein said polymer is a polycarbophil.

15. The composition according to claim 13, wherein said polymer is a Carbopol.

16. The composition according to claim 15, wherein said polymer is Carbopol 974P.

17. The composition according to claim 13, further comprising EDTA.

18. The composition according to claim 1, wherein said aqueous medium has a pH of from 4.0 to 6.5.

19. The composition according to claim 1, wherein said non-steroidal anti-inflammatory agent is contained in an amount of from 0.01 to 5.0% by weight of the entire composition.

20. The composition according to claim 1, further comprising a perborate salt.

21. A method for treating an eye, which comprises administering to an eye in need thereof an effective amount of the composition according to claim 1.

22. A method for making the composition according to claim 1, which comprises:

combining a non-steroidal anti-inflammatory agent and a divalent cation source in an aqueous medium to form a precipitate-containing solution.

23. The method according to claim 22, wherein said non-steroidal anti-inflammatory agent is added to an aqueous solution containing a polymer dispersed therein and said divalent cation source.

24. The method according to claim 23, wherein said aqueous solution further comprises EDTA and said dispersed polymer is a water insoluble, water-swellable crosslinked carboxy-containing polymer.

25. The method according to claim 24, wherein said non-steroidal anti-inflammatory agent comprises diclofenac and said divalent cation source is $CaCl_2$, $MgCl_2$ or $MgSO_4$.

26. The composition according to claim 12, which further comprises EDTA and wherein said divalent cation is provided by a divalent cation source selected from the group consisting of $CaCl_2$, $MgCl_2$ or $MgSO_4$.

27. The composition according to claim 26, wherein said non-steroidal anti-inflammatory agent is diclofenac provided in the form of sodium diclofenac, and wherein said sodium diclofenac is added to an aqueous suspension comprising said divalent cation sources said polymer, and water.

28. The composition according to claim 1, further comprising benzalkonium chloride.

29. An ophthalmic composition comprising an aqueous suspension of a crosslinked carboxyl-containing polymer, solid diclofenac in free-acid form, dissolved diclofenac, and dissolved $Mg^{++}$ or $Ca^{++}$ cations in an amount of from about 1 to 5 times the stoichiometric equivalent amount per mole of said solid diclofenac; said composition having a pH of from about 4.0 to about 6.7 and the total amount of diclofenac being a pharmaceutically effective amount and said solid diclofenac comprising 85 to 95 mol % of the total amount of diclofenac.

30. The composition according to claim 29, further comprising 0.03 to 0.3 wt. % sodium perborate, 0.003 to 0.03 wt. % polyphosphonic acid peroxy stabilizer and 0.01 to 0.1 wt. % EDTA.

31. The composition according to claim 30, wherein said sodium perborate is contained in an amount of about 0.28 wt. % and said polyphosphonic acid peroxy stabilizer is diethylene triamine penta(methylene-phosphonic acid).

* * * * *